(12) United States Patent
Murray et al.

(10) Patent No.: US 8,822,189 B2
(45) Date of Patent: Sep. 2, 2014

(54) THERMOSTABLE ENZYME TECHNOLOGY FOR ALGAL BIOCONVERSION

(75) Inventors: Patrick Murray, Clonlara (IE); Sara Fernandes, Galway (IE); Maria Tuohy, Moycullen (IE)

(73) Assignees: AER Sustainable Energy Limited, Dublin (IE); National University of Ireland, Galway (IE)

( * ) Notice: Subject to any disclaimer, the term of this patent is extended or adjusted under 35 U.S.C. 154(b) by 0 days.

(21) Appl. No.: 13/578,541

(22) PCT Filed: Feb. 8, 2011

(86) PCT No.: PCT/EP2011/051841
§ 371 (c)(1),
(2), (4) Date: Feb. 21, 2013

(87) PCT Pub. No.: WO2011/095643
PCT Pub. Date: Aug. 11, 2011

(65) Prior Publication Data
US 2013/0210083 A1    Aug. 15, 2013

(30) Foreign Application Priority Data

Feb. 8, 2010   (IE) .................................. 2010/0062

(51) Int. Cl.
| | |
|---|---|
| *B65G 25/00* | (2006.01) |
| *C11C 1/00* | (2006.01) |
| *C12P 7/58* | (2006.01) |
| *C12P 7/64* | (2006.01) |
| *C12P 1/04* | (2006.01) |

(52) U.S. Cl.
USPC ........... 435/171; 435/134; 435/137; 435/271; 424/195.17

(58) Field of Classification Search
CPC ................................ D21C 5/005; C11C 1/045
USPC ................... 426/11; 435/171, 137, 134, 271; 424/195.17
See application file for complete search history.

(56) References Cited

U.S. PATENT DOCUMENTS

2010/0028485 A1\*   2/2010   Tuohy et al. .................... 426/11

FOREIGN PATENT DOCUMENTS

WO         2007/091231 A1     8/2007

OTHER PUBLICATIONS

Tuohy, M.G., et al., "Characterization of the Individual Components of the Xylanolytic Enzyme System of Talaromyces Emersonii", Bioresource Technology, vol. 50, No. 1, pp. 37-42, Jan. 1, 1994. (6 pages total).
International Search Report mailed Sep. 22, 2011, issued in connection with corresponding PCT Application No. PCT/EP2011/051841 (3 pages total).

\* cited by examiner

*Primary Examiner* — Maryam Monshipouri
(74) *Attorney, Agent, or Firm* — Ascenda Law Group, P.C.

(57) ABSTRACT

Thermostable enzyme technology for algal bioconversion The present invention relates to thermostable enzyme systems suitable for use in the production of biofuels and bioproducts from algae, and to a method of producing energy feedstocks, stocks, specifically (i) fermentable sugars and (ii) lipid fractions from algae, for the production of biofuels such as bioethanol, biobutanol and bio-oils or biodiesel, as well as other value-added biomolecules (e.g. proteins, peptides, oils, pigments, nucleic acids).

22 Claims, 9 Drawing Sheets

Figure 1 Key exo-hydrolases (IU/mg/g Inducer) in *Talaromyces emersonii* enzyme cocktails

Figure 2 Key endo-hydrolases (IU/mg/g Inducer) in *Talaromyces emersonii* enzyme cocktails Figure 3 Key exo-hydrolases (IU/mg/g Inducer) in the 14 *Talaromyces emersonii* enzyme cocktails produced for microalgal bioconversion.

Figure 4 Key endo-hydrolases (IU/mg/g Inducer) in the 14 *Talaromyces emersonii* enzyme cocktails produced for microalgal bioconversion.

Figure 5 Standard sugar fractionation on Carbopac PA100

Figure 6A Fractionation of the products of hydrolysis of *Dilsea carnosa* (October) by *Talaromyces emersonii* thermozyme cocktail ^.

Figure 6B Fractionation of the products of hydrolysis of *Dilsea carnosa* (October) by *Talaromyces emersonii* thermozyme cocktail*.

Figure 7a Fractionation of the products of hydrolysis of *Laminaria saccharina* (October) by *Talaromyces emersonii* thermozyme cocktail ^.

Figure 7b Fractionation of the products of hydrolysis of *Laminaria saccharina* (October) by *Talaromyces emersonii* thermozyme cocktail *.

Figure 8a GC of chemically extracted (control) *Isochrysis galbana*.

Figure 8b GC of ^ enzyme treated *Isochrysis galbana*.

Figure 8c GC of * enzyme treated *Isochrysis galbana*.

Figure 8d GC of 3 enzyme treated *Isochrysis galbana*.

THERMOSTABLE ENZYME TECHNOLOGY FOR ALGAL BIOCONVERSION

This Application is a 371 of PCT/EP2011/051841, filed Feb. 8, 2011, which claims foreign priority to Irish Application No. 2010/0061 filed Feb. 8, 2010.

FIELD OF THE INVENTION

The present invention relates to thermostable enzyme systems suitable for use in the production of biofuels and bioproducts from algae.

BACKGROUND TO THE INVENTION

Increasing demands on fossil fuel energy reserves, ever increasing energy costs and global warming have led to a heightened interest in alternative fuels. In the near future alternative carbon neutral renewable liquid fuels are required to totally displace decreasing reserves of petroleum-derived transport fuels that contribute to global warming. Biodiesel from oil crops and bioethanol from sugarcane and corn are being produced in increasing amounts as renewable biofuels, but their production in large quantities is not sustainable. To satisfy the biodiesel energy need in the United States (0.53 billion m$^3$), 111 million hectares or 61% of available cropping land would have to be cultivated with oil palm, which is clearly an unrealistic option. Alternative sources of biological starting materials or energy feedstocks are required and may potentially be offered by marine macro/micro-algae. To produce an equivalent amount of biodiesel from microalgal feedstocks would require only 3% of the cropping area of the United States, a much more feasible option and thus the importance of microalgae as an alternative feedstock for biodiesel production becomes obvious. Approximately half of the dry weight of microalgal biomass is carbon-rich and derived from carbon dioxide; production of 100 tonnes of biomass will fix 183 tonnes (approx.) of carbon dioxide. This may come from existing fossil fuel power plants at little or no cost. Ideally microalgal biodiesel could be carbon neutral with the energy required for processing the algae coming from methane produced by anaerobic digestion of biomass left over after the oil has been extracted.

Another important advantage of microalgae is that, unlike oil crops, they grow extremely rapidly and commonly double their biomass within 24 h. In fact, the biomass doubling time for microalgae during exponential growth can be as short as 3.5 h.

Microalgae comprise a vast group of photosynthetic, heterotrophic organisms, which have an extraordinary potential for cultivation as energy crops, converting sunlight, water and carbon dioxide to algal biomass. Microalgae encompass an immense range of genetic diversity and can exist as unicells, colonies and extended filaments. It has been estimated that between 200,000 and several million species of microalgae may exist, compared with about 250,000 species of higher plants. They are ubiquitously distributed throughout the biosphere and grow under the widest possible variety of conditions. Growth media are generally inexpensive, sea water supplemented with commercial nitrate and phosphate fertilizers, and a few other micronutrients can be used for growing marine microalgae. Fresh and brackish water from lakes and rivers can be used for freshwater species. Economics dictates the biomass must be produced at minimal expense, using freely available sunlight and is thereby affected by fluctuations such as daily and seasonal variations in light levels. Microalgae can be grown on a large scale in photo bioreactors.

While the full extent of the global resource of macroalgae is not yet fully known, these significantly larger algae include an equally diverse range of species. More than 60% of the biomass weight of brown, green and red macroalgae (also known as seaweeds) can be comprised of carbohydrate. Specific phycocolloids derived from these macroalgae (e.g. alginates, carageenans, sulphated galactans, agars) have a long history of use in food and pharma applications. These and other carbohydrates present in macroalgae can be converted to fermentable sugars to provide an additional (not sole) feedstock source for biofuel production. However, due to the extensive repertoire of additional high-value molecules (e.g. pigments, polyphenols, protein, oils, minerals, vitamins and trace elements) that are present in the brown, green and red macroalgae, they represent a rich resource of high-value bioproducts.

OBJECT OF THE INVENTION

It is an object of the present invention to provide a method of producing energy feedstocks, specifically (i) fermentable sugars and (ii) lipid fractions from algae, for the production of biofuels such as bioethanol, biobutanol and bio-oils or biodiesel, as well as other value-added biomolecules (e.g. proteins, peptides, oils, pigments, nucleic acids, etc.). It is a further object of the invention to provide such a process, which does not require the pre-treatment of the algal biomass. Generally, for biomass bioconversion a pre-treatment step using a mild acid or alkaline hydrolysis with sulphuric, nitric or phosphoric acid or ammonia solution, respectively, coupled with some type of steam pretreatment are used as a prelude to enzyme action. Alternative pretreatments can include milling and mild thermochemical approaches. The majority of these processes use hazardous chemicals, are often energy intensive, generate potentially hazardous wastestreams and increase the costs involved in bioconversion processes. Thus an object of the invention is to provide a 'green biochemistry' process which reduces the use of hazardous chemicals and which is less expensive to operate. A further object of the invention is to provide an enzyme composition or cocktail, which can be used in the process of producing fermentable sugars, lipid fractions and other value-added co-products from algae.

SUMMARY OF THE INVENTION

The present invention provides a method of producing fermentable sugars and other biomolecules from dried algal biomass (from macroalgae and microalgae) comprising hydrolysing the dried biomass with an enzyme composition, the enzyme composition being derived from *Talaromyces emersonii* which has been grown in the presence of carob powder, or in the presence of a mixture of tea leaves and paper plates, and isolating the sugars from the resultant hydrolysate. The carob powder, tea leaves, paper plates or algae should be present in the growth medium in an amount of about 2% (w/v). Cultures produced solely on algae can also be combined or blended with cultures grown on another low-cost carbon source, e.g. carob powder, tea leaves, paper plates (or a combination thereof) to produce a super-cocktail. Preferably the hydrolysis is carried out for at least 6-12 hours, and more preferably for at least 18-24 hours. Suitably a ratio of enzyme to algae of 0.5 mL unconcentrated enzyme system is used for every 50 mg algae (dry weight).

The algal biomass may be selected from the group comprising brown, green and red macroalgae, including *Laminaria saccharina*, *Sargussum* sp., *Palmaria palmata* and *Dilsea carnosa*, as well as microalgae. Preferably *Laminaria* spp. including *L. saccharina*, *L. digitata*, *L. hyperborea*, etc. and microalgae, which have been harvested in the autumn are hydrolysed. *Dilsea carnosa* shows no seasonal variation and so can be harvested for processing at any time of the year. *Ulva* sp. show seasonal variation in the late autumn and winter periods and are best harvested in the later spring to early autumn for processing.

The hydrolysis is carried out at 65 to 70° C., preferably at 67° C.

The hydrolysis is carried out at pH 4 to 5, preferably at pH 4.5 for macroalgae or in water ($H_2O$) for microalgae.

Suitably, hydrolysis is carried out using 5-1,500 mg dried seaweed, with no pre-treatment step, with 0.5-5.0 mL ammonium acetate buffer pH 4.5 (or 0.5-5.0 mL $H_2O$) and 0.5-5.0 mL of suitably diluted enzyme composition and incubated for 6-24 h at 65-67° C. at 120 rpm. The invention also provides an enzyme composition for use in the hydrolysis of algal biomass derived from *Talaromyces emersonii* which has been grown in the presence of carob powder, or in the presence of a mixture of tea leaves and paper plates, or in the presence of either macro- or micro-algal biomass.

DETAILED DESCRIPTION OF THE DRAWINGS

Method 1
Large Scale Cultures for Bioconversion of Seaweed (Macroalgae) were Prepared as Follows:

A total of 3-4 1 cm² pieces of mycelial mat from the outer growing edges of a 3-5 day old *T. emersonii* Sabouraud dextrose agar (SDA) plate culture were transferred to liquid medium containing 2% glucose (w/v) as the sole carbon source. The culture was grown at 45° C. and 220 rpm for 36 h at 45° C. and then a 10% (v/v) transfer to an identical medium (400 mL) was grown for a further 36 h prior to transfer to a defined medium containing an enzyme inducing carbon source (a) carob powder and (b) tea leaves/paper plates as sole carbon (or algae). The fungal cells were cultured for 72 h and used as inocula for a further liquid cultivation (5% of each v/v) of *T. emersonii* in medium containing carob, tea leaves/paper plates, or 2% (w/v) macroalgal seaweed samples (dried and ground in a Waring blender) as sole carbon source under identical cultivation conditions. Seaweeds used as sole carbon sources were:

Brown Seaweeds
  1 (a & b) *Laminaria hyperborea* harvested in April (a) and October (b) 2004
  2 (a & b) *Laminaria saccharina* harvested in April (a) and October (b) 2004
  3 (a, b & C) *Ascophylum nodosum* harvested in April (a), September (b) and October (c) 2004
  4 (a & b) *Himanthalia elongata* harvested in April (a) and October (b) 2004
  5 (a & b) *Fucus serratus* harvested in April (a) and October (b) 2004
  6 (a & b) *Pelvetia caniculata* harvested in April (a) and October (b) 2004
  7 (a & b) *Laminaria digitata* harvested in April (a) and September (b) 2004
  8 (a & b) *Alaria esculenta* harvested in April (a) and October (b) 2004
  16 *Sargussum* sp. (grass; Portugal).
Red Seaweeds
  9 (a & b) *Palmaria palmata* harvested in April (a) and October (b) 2004
  10 (a & b) *Chondrus crispus* harvested in April (a) and October (b) 2004
  11 (a & b) *Porphyra* sp. harvested in April (a) and October (b) 2004
  12 (a & b) *Polysiphonia lanosa* harvested in April (a) and October (b) 2004
  17 (a & b) *Dilsea carnosa* harvested in April (a) and October (b) 2004
  13 (a & b) *Mastocarpus stellatus* (carrageenen) harvested in April (a) and October (b) 2004
Green Seaweeds
  14 (a & b) *Ulva* sp. harvested in April (a) and October (b) 2004
  15 (a & b) *Enteromorpha* sp. harvested in April (a) and October (b) 2004.

After 4 days growth in individual seaweeds the cultures were transferred (10% v/v) to identical media supplemented with an identical concentration (2% w/v) of the same seaweed and grown for a further 4 days; this process was repeated for 5 further transfers or passes. After each transfer/pass the culture liquid was harvested by centrifugation and stored as individually induced seaweed enzyme mixtures and stored at −20° C. Therefore 5 *Talaromyces emersonii* enzyme cocktails induced by each of the 17 seaweeds inducers were produced, analysed and used to generate 4 super-cocktails as set out below. The passes represent a pressure on the fungus to adapt to the carbon source presented. Effectively the fungus needs to generate an enzyme system capable of breaking down the substrate presented to it. This takes time or an adaption period, so the first generation of fungal cells recognise a carbon source and try to produce an enzyme system capable of hydrolysing it. The new cells produced in the second pass then have an advantage as they arise from cells from the first pass which have begun to produce a system capable of degrading the substrate. As the passes proceed, the new cells become optimised for production of an enzyme system more capable of hydrolysing the substrate.

(^) Enzyme Cocktail
  1 ml (Seaweed 2 Pass 1)+1 mL (Seaweed 2 Pass 3)+1 mL (Seaweed 9 Pass3)+1 mL (Seaweed 10 Pass 3)+1 mL (Seaweed 13 Pass 3)+1 mL (Seaweed 14 Pass 3)+1 mL (Seaweed 17 Pass 4)+21 mL 100 mM ammonium acetate, pH 5.0
(9) Enzyme Cocktail 2.5 mL (Seaweed 9 Pass 3)+2.5 mL (Seaweed 9 Pass 5)+15 mL 100 mM ammonium acetate, pH 5.0
(*) Enzyme Cocktail
6.25 mL Carob powder induced (120 h)+6.25 mL Tea leaves/Paper plates induced (120 h)+37.5 mL 100 mM ammonium acetate, pH 5.0
(3) Enzyme Cocktail
12.5 mL sugar beet pulp/sorghum induced *Talaromyces emersonii* enzyme system (120 h)+37.5 mL 100 mM ammonium acetate, pH 5.0

Large Scale Cultures for Bioconversion of Microalgae were Prepared as Follows:

A total of 3-4 1 cm$^2$ pieces of mycelial mat from the outer growing edges of a 3-5 day old *T. emersonii* Sabouraud dextrose agar (SDA) plate culture were transferred to liquid medium containing 2% glucose (w/v) as the sole carbon source. The culture was grown at 45° C. and 220 rpm for 36 h at 45° C. and used to 'seed' or inoculate [5% (v/v) transfer] a new batch of an identical medium (200-400 mL), which was grown for a further 36 h. This 'seed' culture was used to inoculate a defined medium containing 0.25-2.0% (w/v) of the appropriate enzyme inducing carbon source(s). A total of 14 novel enzyme cocktails were generated using the combinations of carbon sources (correspondingly numbered 1-14) listed below:

1. Seaweed 2/wheat bran/tea leaves
2. Sorghum/wheat bran
3. Sorghum and olive oil
4. Seaweed 2 with yeast extract being replaced by peptone in media
5. Oat spelt xylan and oleic acid
6. Seaweed 9
7. Seaweed 9 and olive oil
8. Tea leaves and paper plates and oleic acid
9. Seaweed 9/sorghum and olive oil
10. Casein and wheat bran
11. Seaweed 2/wheat bran/tea leaves and oleic acid
12. Microalgae 1/Microalgae 5/Microalgae 7
13. Microalgae 2/Microalgae 5/Microalgae 7
14. A fixed amount of each of seven individual microalgal samples The fungal cells were cultured for 36-48 h and used as inocula for a further liquid cultivation (5% v/v) of *T. emersonii* in individual media (400-1,500 mL) containing the carbon sources listed 1-14 above, under identical cultivation conditions.

Method 1 Results

Figure 1:
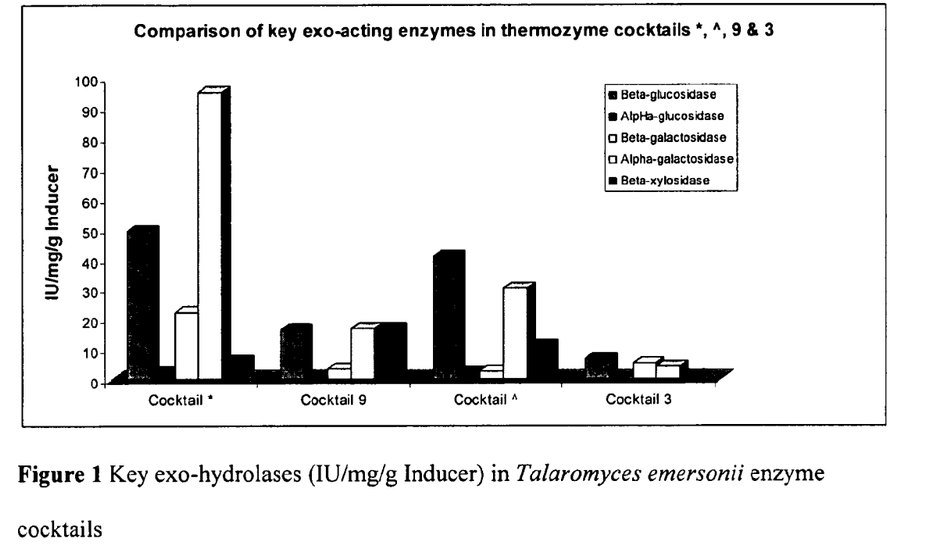
FIG. 1 Key exo-hydrolases (IU/mg/g Inducer) in *Talaromyces emersonii* enzyme cocktails for seaweed (macroalgae) conversion FIG. 2 Key endo-hydrolases (IU/mg/g Inducer) in *Talaromyces emersonii* enzyme cocktails for seaweed (macroalgae) conversion FIG. 3 Key exo-hydrolases (IU/mg/g Inducer) in *Talaromyces emersonii* enzyme cocktails for microalgae conversion FIG. 4 Key endo-hydrolases (IU/mg/g Inducer) in *Talaromyces emersonii* enzyme cocktails for microalgae conversion FIG. 5 Standard sugar fractionation on Carbopac PA100
Figure 2:
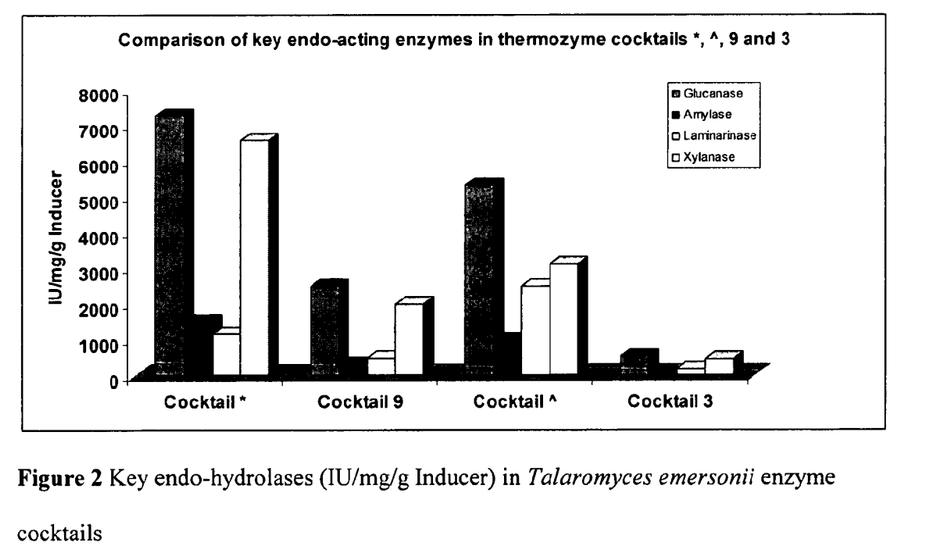
Figure 3:
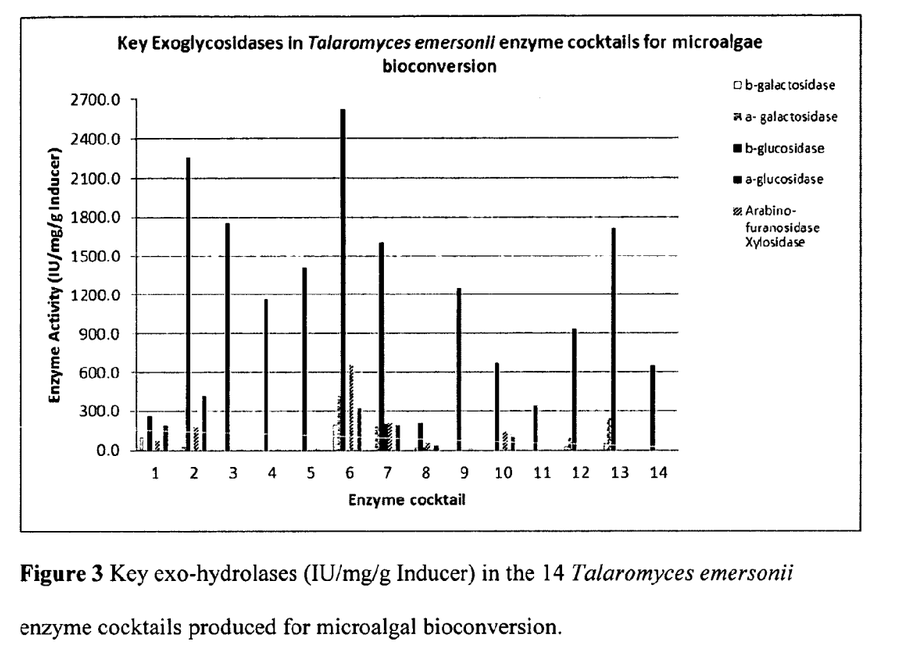
Figure 4:
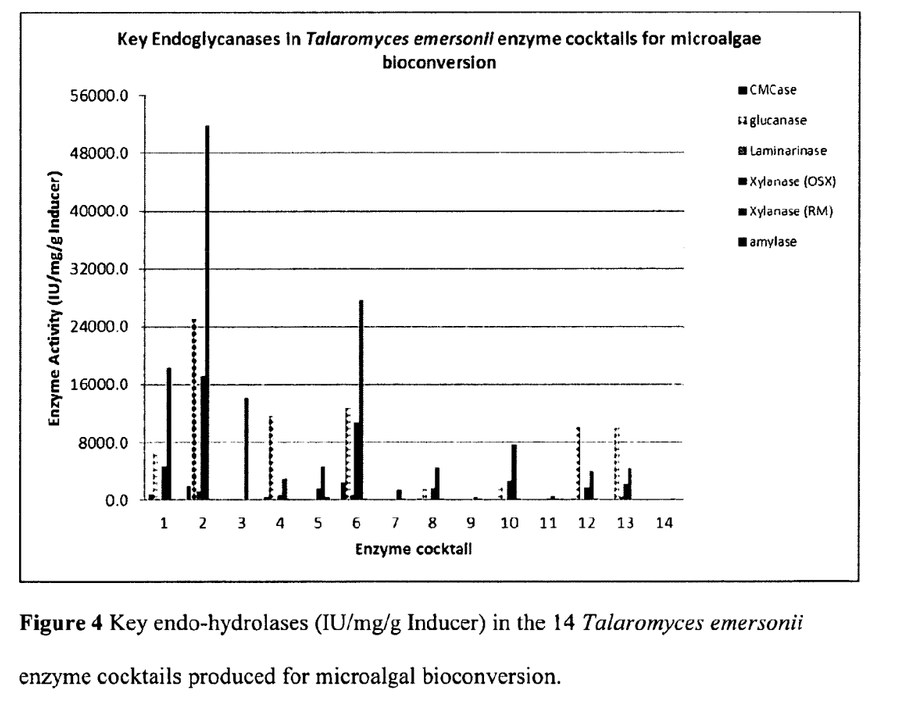
Figure 5:
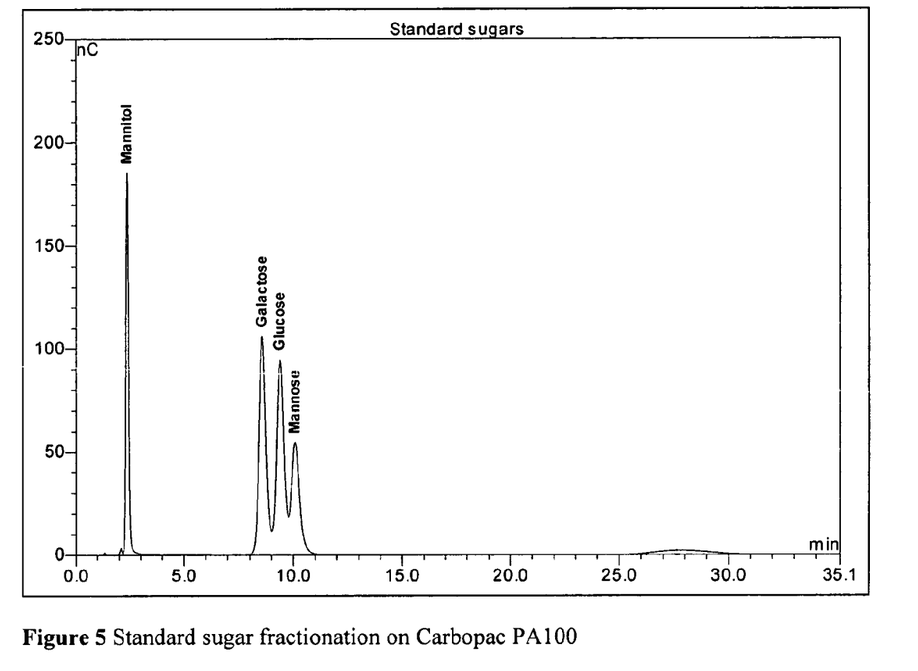
Figure 6A:
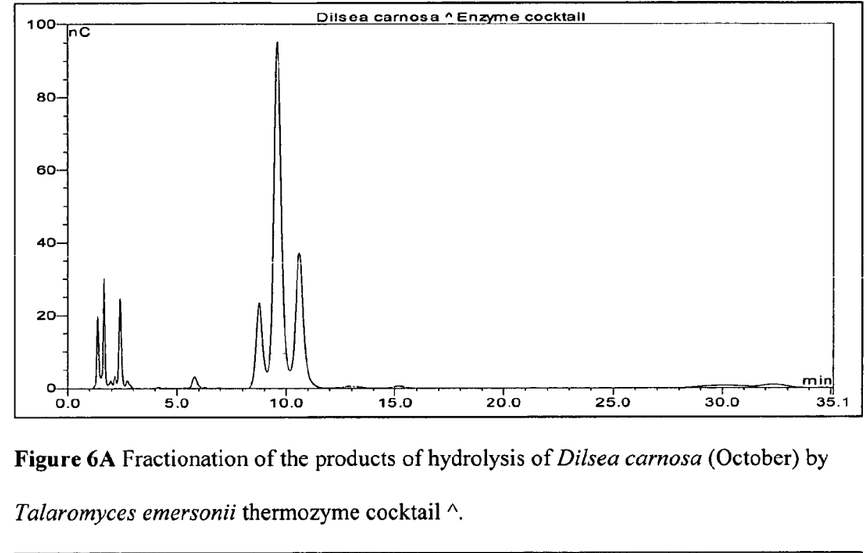
FIG. 6a-6b Fractionation of the products of hydrolysis of *Dilsea carnosa* (October) by *Talaromyces emersonii* thermozyme cocktails ^ and *, respectively.
Figure 6B:
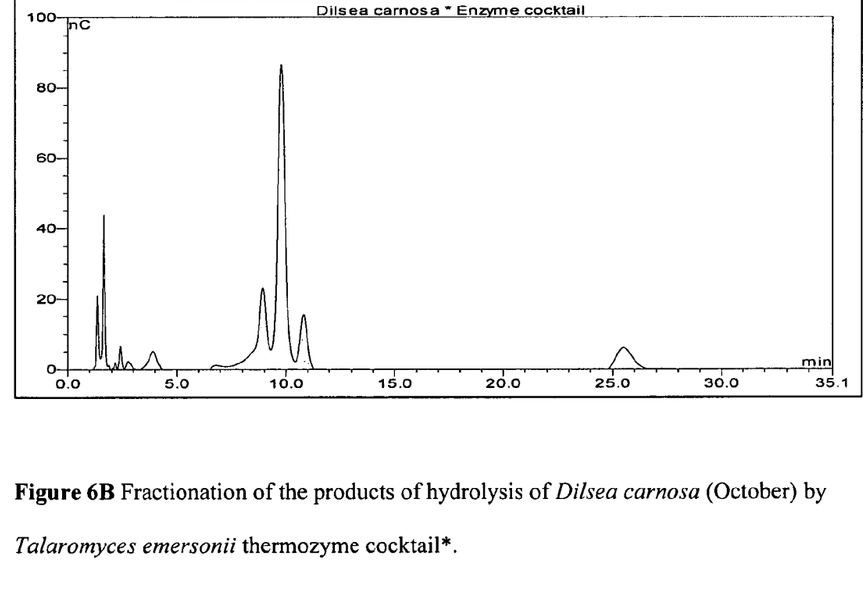
Figure 7A:
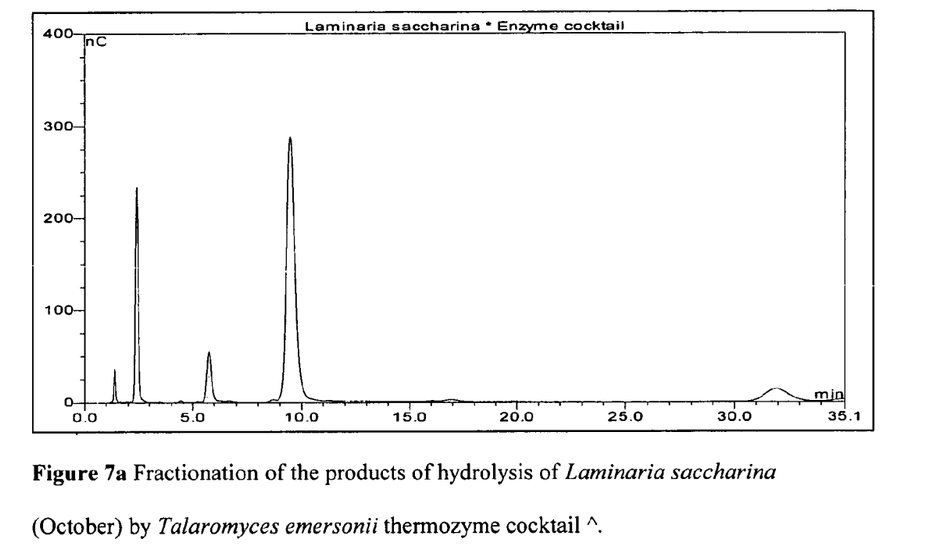
FIG. 7a-7b Fractionation of the products of hydrolysis of *Laminaria saccharina* (October) by *Talaromyces emersonii* thermozyme cocktails ^ and *, respectively.
Figure 7B:
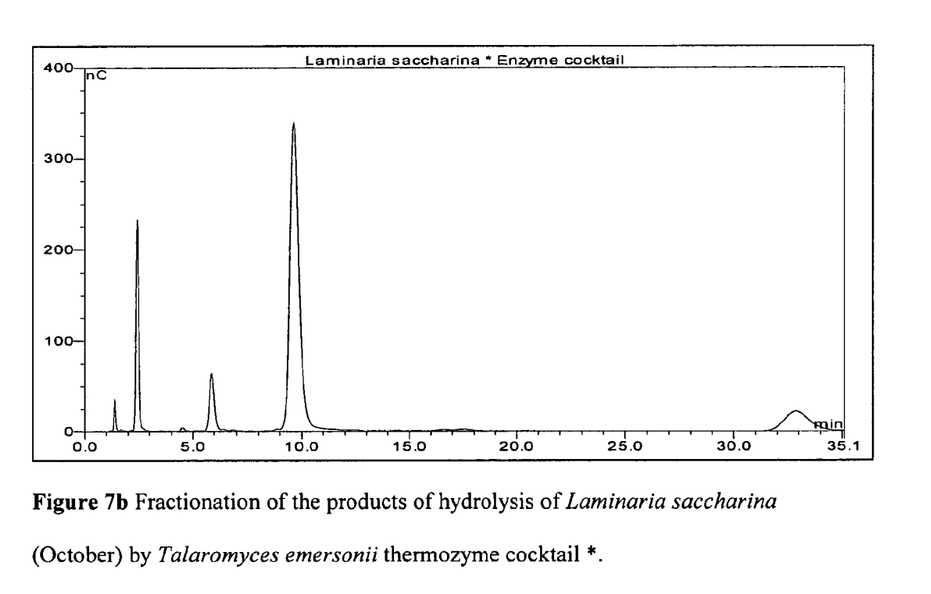
Figure 8A:
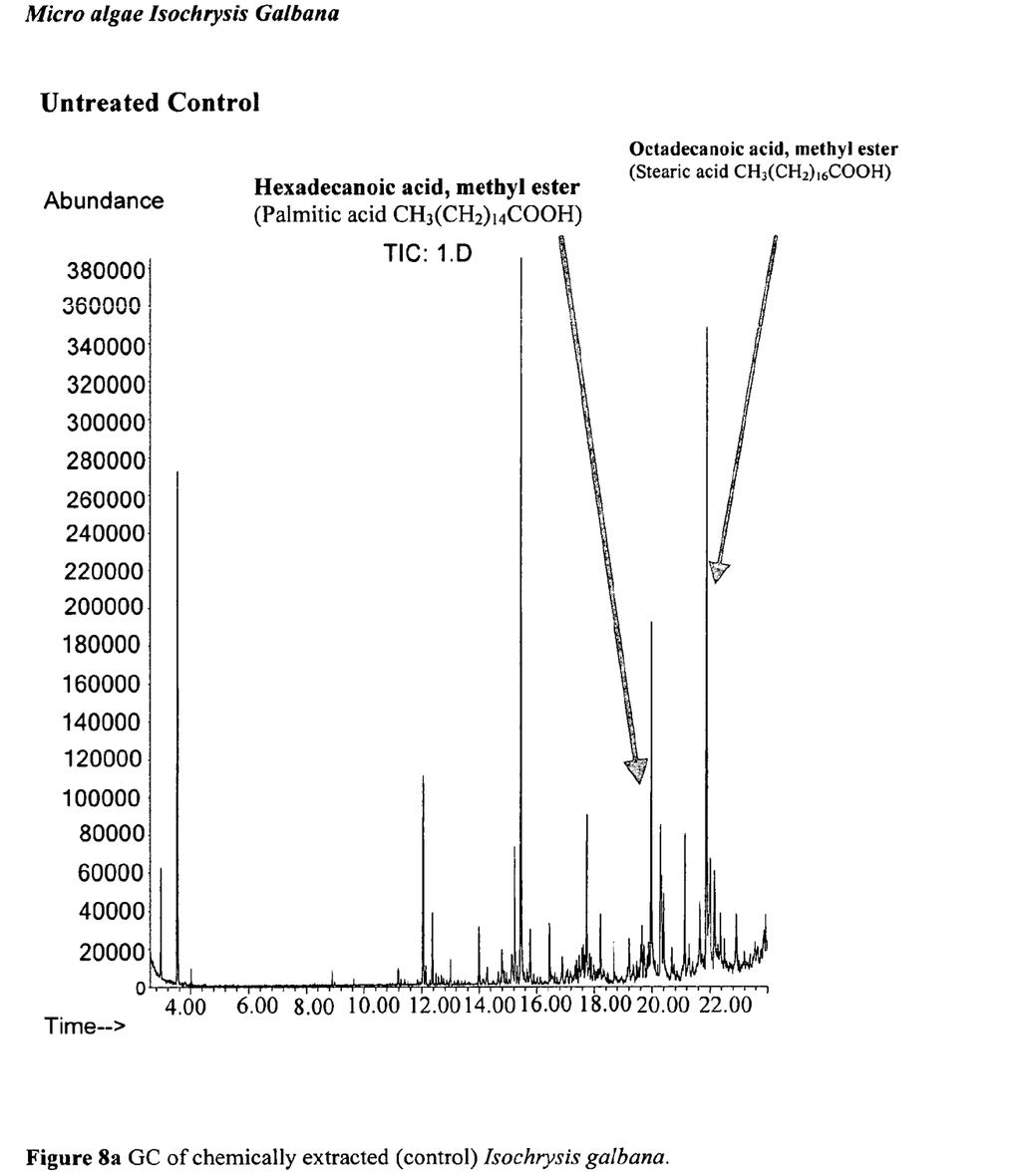
FIG. 8a-8d GC of chemically extracted (control) and enzyme treated *Isochrysis galbana*, respectively.
Figure 8B:
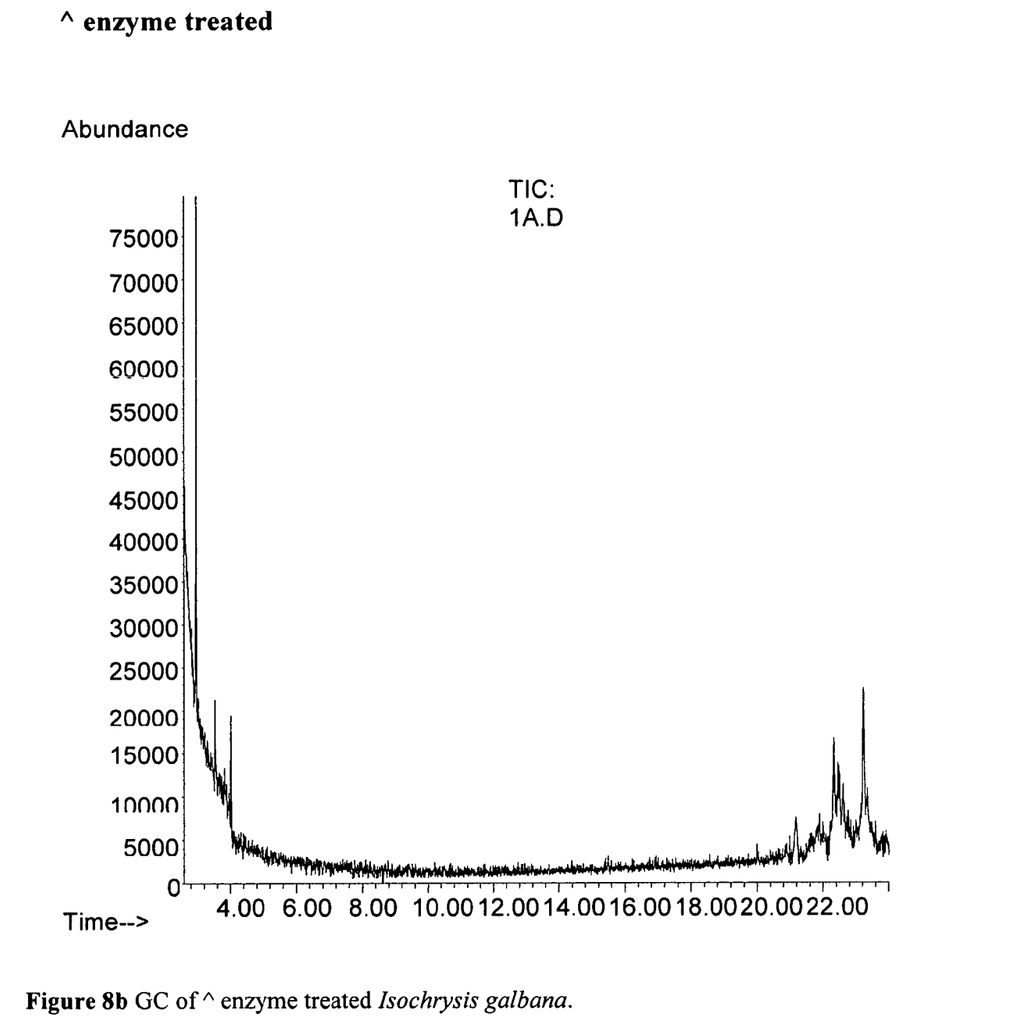
Figure 8C:
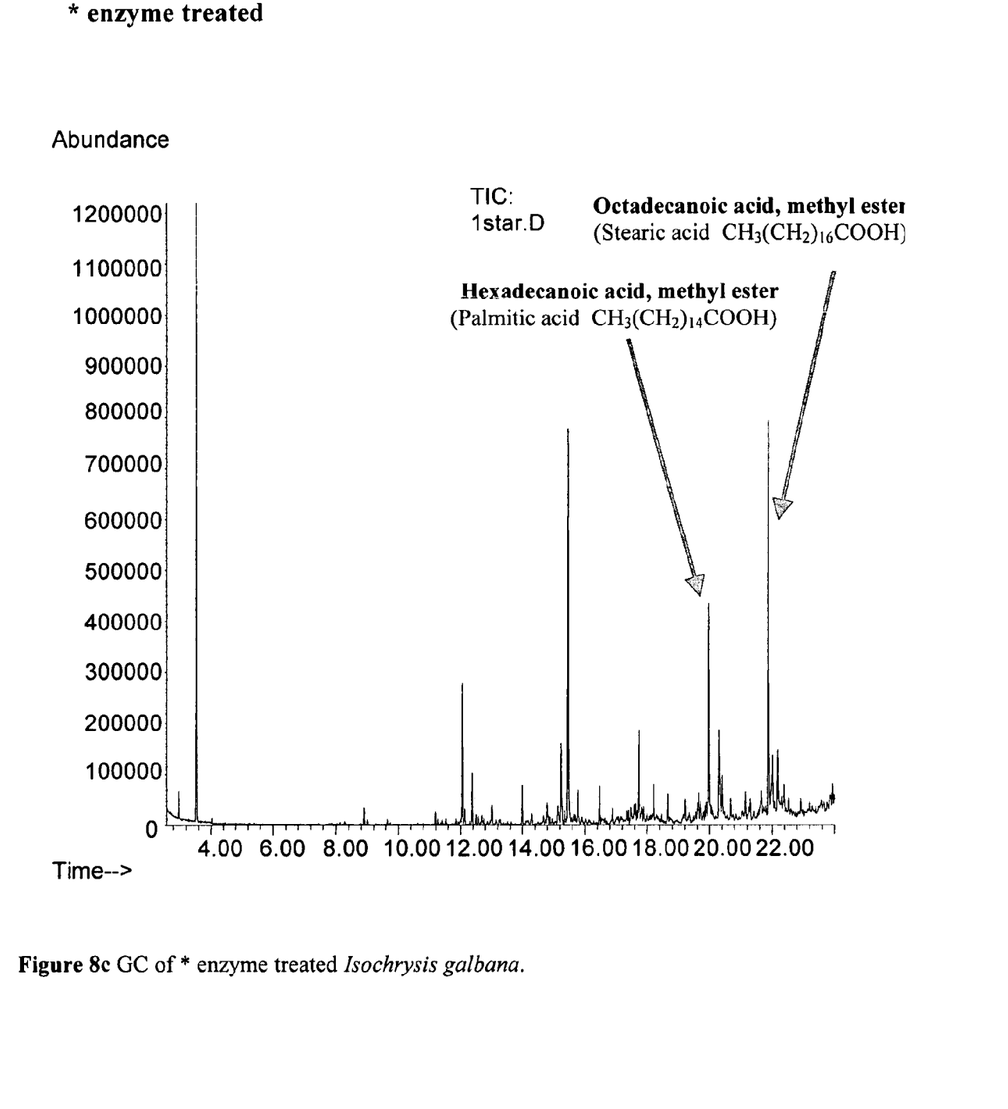
Figure 8D:
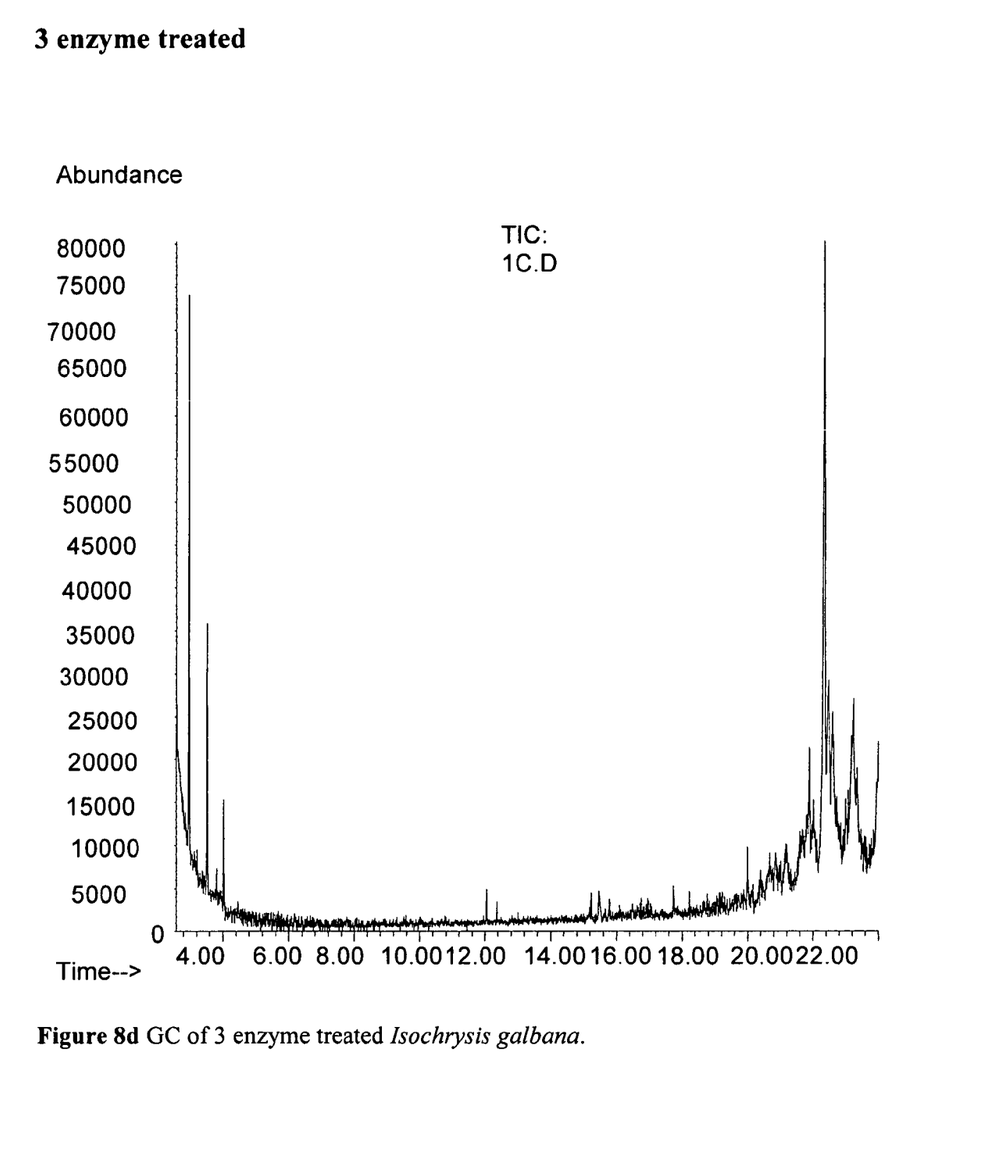

An analysis of the individual cocktails for key exo and endo-acting hydrolytic enzyme activities relevant to biopolymer hydrolysis in macroalgae are graphed (FIGS. 1 and 2) and tabulated (Tables 1 and 2) below. Similarly, the key exo and endo-acting hydrolytic enzyme activities in the 14 cocktails generated for bioconversion of microalgae are tabulated in Tables 3 and 4 and graphed in FIGS. 3 and 4.

TABLE 1

Composition of the key *Talaromyces emersonii* enzyme cocktails with respect to the % of key exo-hydrolases present for bioconversion of macroalgae

|  | Cocktail * | Cocktail ^ | Cocktail 9 | Cocktail 3 |
|---|---|---|---|---|
| β-Glucosidase | 28 | 43 | 30 | 41 |
| α-Glucosidase | 1 | 2 | 2 | 0 |
| β-Xylosidase | 14 | 4 | 8 | 33 |
| α-Galactosidase | 54 | 34 | 30 | 25 |
| β-Galactosidase | 3 | 17 | 30 | 1 |

TABLE 2

Composition of the key *Talaromyces emersonii* enzyme cocktails with respect to the % of key endo-hydrolases present for bioconversion of macroalgae

|  | Cocktail * | Cocktail ^ | Cocktail 9 | Cocktail 3 |
|---|---|---|---|---|
| Glucanase | 43 | 46 | 44 | 47 |
| Xylanase | 41 | 25 | 38 | 47 |
| Laminaranase | 7 | 22 | 11 | 6 |
| Amylase | 9 | 7 | 7 | 0 |

TABLE 3

Composition of the 14 *Talaromyces emersonii* enzyme cocktails with respect to the % of key exo-hydrolases present for bioconversion of microalgae

|  | β-galactosidase | α-galactosidase | β-glucosidase | α-glucosidase | Arabino-furanosidase | Xylosidase | CBH (Cell) |
|---|---|---|---|---|---|---|---|
| Cocktail 1 | 12.6 | 0.0 | 33.2 | 0.0 | 9.2 | 20.3 | 24.6 |
| Cocktail 2 | 0.0 | 0.8 | 68.0 | 0.0 | 5.4 | 13.3 | 12.5 |
| Cocktail 3 | 0.0 | 0.0 | 96.5 | 0.0 | 0.0 | 3.5 | 0.0 |
| Cocktail 4 | 0.0 | 0.0 | 98.9 | 0.0 | 0.0 | 1.1 | 0.0 |
| Cocktail 5 | 0.0 | 0.0 | 99.0 | 0.0 | 0.0 | 1.0 | 0.0 |
| Cocktail 6 | 4.2 | 9.0 | 57.0 | 0.0 | 14.3 | 8.5 | 7.0 |
| Cocktail 7 | 0.0 | 7.0 | 60.3 | 7.6 | 7.9 | 9.9 | 7.2 |
| Cocktail 8 | 0.0 | 5.4 | 50.1 | 5.5 | 13.5 | 16.9 | 8.7 |
| Cocktail 9 | 0.0 | 0.0 | 98.8 | 0.0 | 0.0 | 1.2 | 0.0 |
| Cocktail 10 | 0.0 | 0.2 | 65.0 | 0.0 | 13.5 | 11.4 | 9.9 |
| Cocktail 11 | 0.0 | 0.0 | 100.0 | 0.0 | 0.0 | 0.0 | 0.0 |
| Cocktail 12 | 2.2 | 8.9 | 86.6 | 0.0 | 0.0 | 2.3 | 0.0 |
| Cocktail 13 | 2.5 | 11.6 | 82.2 | 0.0 | 0.0 | 3.6 | 0.0 |
| Cocktail 14 | 0.0 | 0.0 | 99.2 | 0.0 | 0.0 | 0.0 | 0.8 |

TABLE 4

Composition of the 14 *Talaromyces emersonii* enzyme cocktails with respect to the % of key endo-hydrolases present for bioconversion of microalgae

|  | CMCase | Glucanase | Laminarinase | Xylanase (OSX) | Xylanase (RM) | amylase | Galactanase (LWAG) |
|---|---|---|---|---|---|---|---|
| Cocktail 1 | 2.5 | 21.2 | 0.1 | 15.2 | 60.8 | 0.1 | 0.0 |
| Cocktail 2 | 1.9 | 25.8 | 1.1 | 17.6 | 53.3 | 0.2 | 0.0 |
| Cocktail 3 | 0.0 | 0.0 | 1.7 | 0.0 | 98.1 | 0.0 | 0.2 |
| Cocktail 4 | 2.4 | 71.1 | 1.8 | 4.0 | 18.1 | 1.2 | 1.3 |
| Cocktail 5 | 0.0 | 0.0 | 0.0 | 24.3 | 70.4 | 5.4 | 0.0 |
| Cocktail 6 | 4.3 | 23.5 | 1.2 | 19.8 | 51.0 | 0.2 | 0.0 |
| Cocktail 7 | 0.0 | 0.0 | 0.0 | 0.0 | 95.5 | 4.5 | 0.0 |
| Cocktail 8 | 0.8 | 19.6 | 0.1 | 20.3 | 58.8 | 0.2 | 0.1 |
| Cocktail 9 | 0.0 | 0.0 | 0.0 | 0.0 | 95.2 | 4.8 | 0.0 |
| Cocktail 10 | 0.0 | 16.2 | 0.1 | 21.3 | 62.3 | 0.1 | 0.0 |
| Cocktail 11 | 0.0 | 0.0 | 1.3 | 15.2 | 74.8 | 0.4 | 8.3 |
| Cocktail 12 | 1.0 | 62.5 | 1.5 | 10.3 | 24.2 | 0.4 | 0.0 |
| Cocktail 13 | 0.0 | 58.6 | 2.8 | 13.0 | 25.6 | 0.0 | 0.0 |
| Cocktail 14 | 0.0 | 0.0 | 63.5 | 0.0 | 0.0 | 36.5 | 0.0 |

Method 2
Algal Hydrolysis Experiments
Bioconversion of Macroalgae:

Hydrolysis was carried out using 5-50 mg dried seaweeds (no pretreatment) with 0.5 mL buffer ammonium acetate buffer pH 4.5 and 0.5 ml of suitably diluted preparations of the individual enzyme systems Cocktail(^) Cocktail (9), Cocktail (3) and (*) Cocktail and incubated for 24 h at 67° C. at 120 rpm. At timed intervals samples were withdrawn from the hydrolysates of the individual seaweeds and analysed for fermentable sugars using a Carbopac PA-100 column fitted to an Ion Chromatographic System with an 18 mM sodium hydroxide gradient. Chromatograms were analysed using Chromeleon (Dionex Corporation Software). Extensive analysis showed that two seaweed samples *Dilsea carnosa* and *Laminaria saccharina* yielded the greatest quantities of simple sugar per unit biomass and were the best substrates for hydrolysis and production of fermentable sugars. The best enzyme systems were identified as the *T. emersonii* (*) and (^) cocktails.

Bioconversion of Microalgae:

Hydrolysis was carried out using individual (replicate) amounts of 5-1,500 mg dried microalgae (no pretreatment) with 0.5-5.0 mL $H_2O$ and 0.5-5.0 mL of suitably diluted preparations of the individual enzyme systems, cocktails 1-14 inclusive, and incubated for 6-24 h at 65-67° C. at 120 rpm. At timed intervals samples were withdrawn from the hydrolysates of the individual microalgae and analysed for (i) fermentable sugars using HPAEC on a Dionex system, as described above, (ii) solvent-recoverable lipid by gravimetric analysis, (iii) protein released using a combination of total nitrogen analysis on a Leco analyser (conversion factor used to estimate protein content) and (iv) pigment released (i.e. chlorophyll a and carotenoids).

Standard NREL acid extraction methods were used to solubilise all carbohydrates present in each algal biomass sample. The carbohydrate contents of the fractions obtained were determined using the Dubois method for total carbohydrate estimation (Dubois et al 1956). A standard gravimetric method was used to determine the lipid content of the 7 microalgal samples. This method involved chloroform-methanol extraction with recovery of lipid from the lower chloroform layer, following removal of the upper methanol phase and the intermediate solid, particulate layer. Aqueous-methanol washes were used to remove any residual water-miscible substances from the lipid-rich fraction. The washed lower phase was transferred to pre-weighed glass bottles and residual chloroform was evaporated prior to weighing the bottles. All analyses were conducted in triplicate. The weight recorded (lipid) was expressed as a % of the total dry microalgal weight in each initial sample. Total protein content (% of the total dry microalgal weight in each initial sample) was determined as total nitrogen protein using a Leco analyser. Pigment content was determined spectrophotometrically following chloroform extraction of pigments present in each of the 7 microalgal biomass samples.

Method 2 Results
Bioconversion of Macroalgae:

Hydrolysis % of the larger scale experiments with *Dilsea carnosa* showed 33-34% hydrolysis by dry weight. Both thermozyme cocktails were effective. Given the polysaccharide content is approximately 50% by dry weight this reflects very high conversion rate of approximately 70%. The principal products of hydrolysis were galactose (13-21%), glucose (60%) and mannose (10-17%) with a small amount of mannitol (4-10%) produced.

Larger scale hydrolysis studies of *Laminaria saccharina* resulted in 34% hydrolysis by dry weight and a theoretical yield of 66% conversion based on carbohydrate composition of dry weight starting material. The principal hydrolysis product was glucose (77-83%) with smaller but appreciable amounts of mannitol (not fermentable by *Saccharomyces cervisiae*) also produced 17-23%.

Bioconversion of Microalgae:

Bioconversion of microalgae was measured by determining microalgal cell rupturing activity (monitored by measuring % pigment release), and the % Lipid, Carbohydrate and Protein released relative to the relative amounts of each biomolecule type in the starting microalgal biomass. The relative amounts of Lipid, Carbohydrate, Protein and Pigment present in each of the 7 microalgae were determined as a % relative to the dry weight of the starting microalgal biomass (see Table 5).

TABLE 5

Lipid, Carbohydrate, Protein and Pigment contents (% Dry weight) of 7 Microalgae species

| Microalgae | Lipid (%) | Carbohydrate (%) | Protein (%) | Pigment (%) |
|---|---|---|---|---|
| Microalgae 1 | 29.6 | 5.94 | 39.53 | 0.93 |
| Microalgae 2 | 9.25 | 6.12 | 33.28 | 0.44 |
| Microalgae 3 | 29.8 | 6.47 | 33.28 | 0.25 |
| Microalgae 4 | 30.75 | 7.12 | 21.09 | 0.25 |
| Microalgae 5 | 36.6 | 6.84 | 38.21 | 0.36 |

TABLE 5-continued

Lipid, Carbohydrate, Protein and Pigment contents
(% Dry weight) of 7 Microalgae species

| Microalgae | Lipid (%) | Carbohydrate (%) | Protein (%) | Pigment (%) |
|---|---|---|---|---|
| Microalgae 6 | 35.9 | 7.75 | 26.87 | 0.40 |
| Microalgae 7 | 26.8 | 9.27 | 5.49 | 0.28 |

The relative hydrolysis of each individual biomolecule, as a % of the amount present in the initial microalgal biomass (see Tables 6-7 below).

Pigment release reflects cell-rupturing capability. Five enzyme cocktails (1, 2, 6, 8 and 10) effected complete release of all pigment present in Microalgae 1, while 9 cocktails released ≥60% of the available pigment. Three cocktails released ≥60% of the available pigment in Microalgae 2, while 4 and 6 cocktails effected the same extent of pigment release from Microalgae samples 4 and 6, respectively.

As shown in Table 6, Cocktails 1 and 4 released the highest levels of carbohydrate from Microalgae 1. Enzyme cocktail 4 yielded the carbohydrate conversion (72%) from Microalgae 2, while cocktails 4, 6, 9, 10 and 13 released approximately 50% or above of the available carbohydrate from the same algal biomass. All cocktails performed very well with the Microalgae 4 sample and ~99% of the biomass carbohydrate was released by all but 4 enzyme cocktails. Significant release of carbohydrate from Microalgae 6 was obtained with cocktails 1, 2, 3, 4, 6, 7, 8, 11 and 12, with cocktail 7 giving the best performance in terms of carbohydrate release (70.8%).

TABLE 6

Thermozyme cocktail catalysed Carbohydrate release: % of that available in different Microalgal biomass types

| Enzyme Cocktail | Microalgae 1 | Microalgae 2 | Microalgae 3 | Microalgae 4 | Microalgae 5 | Microalgae 6 |
|---|---|---|---|---|---|---|
| 1 | 74.5 | 25.6 | 55.8 | >99.0 | 18.5 | 51.2 |
| 2 | 36.1 | 21.0 | 41.2 | >99.0 | 25.1 | 64.5 |
| 3 | 2.1 | 50.9 | 23.7 | >99.0 | 11.7 | 56.4 |
| 4 | 50.6 | 72.0 | 35.3 | >99.0 | 22.9 | 55.7 |
| 5 | 0.0 | 0.0 | 56.7 | >99.0 | 3.7 | 0.0 |
| 6 | 3.5 | 47.4 | 36.5 | 78.9 | 21.2 | 58.2 |
| 7 | 0.0 | 7.4 | 26.2 | 86.8 | 5.6 | 70.8 |
| 8 | 27.3 | 14.1 | 24.1 | 59.3 | 4.4 | 60.9 |
| 9 | 0.0 | 47.7 | 7.7 | 95.3 | 3.4 | 12.9 |
| 10 | 0.0 | 51.2 | 33.7 | >99.0 | 28.8 | 19.7 |
| 11 | 4.8 | 43.8 | 39.1 | >99.0 | 18.1 | 57.2 |
| 12 | 24.5 | 7.5 | 26.8 | 62.5 | 13.1 | 47.6 |
| 13 | 29.9 | 55.8 | 24.7 | >99.0 | 13.7 | 43.6 |
| 14 | 3.6 | 3.4 | 23.1 | >99.0 | 11.6 | 28.1 |

Table 7 shows protein released as a % of the total available in each individual microalgal biomass sample. The data presented reflect relatively intact protein (relatively unhydrolysed protein).

TABLE 7

Thermozyme cocktail catalysed Protein release:
% of that available in different Microalgal biomass types

| Algal sample | % Protein released |
|---|---|
| Microalgae 1 | 36.0-36.1 |
| Microalgae 2 | 30.7-31.6 |
| Microalgae 3 | 36.8-43.3 |
| Microalgae 4 | 44.3-54.5 |
| Microalgae 6 | 40.6-45.9 |

The release of lipids was quantified using the gravimetric method. During enzyme treatment, complex lipids can be converted to free fatty acids, which are very volatile and cannot be accurately measured using the gravimetric method. Using the gravimetric method, the enzymes released as much as 80-90% of available lipid, which included 45-50% solvent-recoverable lipid as well as fatty acids of biofuel and neutraceutical potential. Cocktails 1, 3, 4, 5, 6, 7, 8, 11 and 13 were particularly effective, with the different cocktails displaying some preferential effects against specific microalgae.

Microalgal Oil Extraction from *Talaromyces emersonii* Treated Samples and GC Analysis Method 3 Control Untreated Microalgae A 5-1500 mg (equivalent) quantity of lyophilized untreated microalgae was placed either in replicate 2.0 mL micocentrifuge tubes and 0.16 mL water, 0.40 mL methanol and 0.20 mL chloroform were added, or for larger quantities, in larger volume tubes (50 mL) with the appropriate volumes of water, methanol and chloroform. The solution was mixed using a vortex for 30 s and then the tubes were placed in an ultrasonic bath at room temperature for 15 min. An additional volume of chloroform and water were added and the contents of the tubes mixed using a vortex mixer for 30 s. The tubes were centrifuged at 3500×g for 15 min. The upper (water+methanol) layer was withdrawn using a pasteur or micro-pipette and the lower chloroform phase containing the extracted lipids was transferred into a new clean glass tube. The solid material left at the bottom of extraction tube was re-extracted two further times with the same procedure and the chloroform phases were combined and then filtered through Whatman No. 1 filter paper pre-saturated with chloroform. The solvent was evaporated at 60° C. to leave the lipids present in the lower phase.

Enzyme Hydrolysates

A 0.25-5 mL volume (5-100 mg equivalent) of each enzyme hydrolysate was extracted with Chloroform (0.3125-6.25 mL):Methanol (0.625-12.5 mL) and mixed using a vortex until the solution appeared homogeneous (one continuous phase). Chloroform (0.3125-6.25 mL) was then added and the sample mixed again before addition of deionized water (0.3125-6.25 mL). The samples were then centrifuged at 2000 rpm to separate the phases; lipids were present in the lower phase, which was stored after evaporation of the solvent at 60° C. Total chloroform-methanol extractable lipid was determined gravimetrically as a % of the total present in the biomass.

Lipid Derivatisation and Analysis

Lipids produced from both control and enzyme treated microalgae were dissolved in toluene (1 mL) and the mixture was left overnight in a stoppered tube at 50° C. Water (5 mL) containing sodium chloride (5%) was added and the required esters were extracted with hexane (2×5 mL), using Pasteur pipettes to separate the layers. The hexane layer was washed with water (4 mL) containing potassium bicarbonate (2% w/v) and dried over anhydrous sodium sulfate. The solution was filtered to remove the drying agent, and the solvent was removed in a stream of nitrogen. Dried derivitised FAME's were dissolved in 1 mL chloroform and analysed by Gas Chromatography-Mass Spectrophotometry. Compounds present in the lipid sample were separated on the capillary GC column and peak fractions analysed and putatively identified from their molecular weight and disintegration pattern with reference to a MS chemical database Method 3 Results Methyl esters of Hexa-, and Octo-decanoic acid were identified. Comparison of the Fatty acid methyl esters (FAMEs) identifiable in the directly extracted and enzyme-treated *Iso-*

*chrysis galbana* microalgae show that the * enzyme-treated alga presents a very similar GC profile to the chemically extracted alga while alga treated with ˆ and 3 cocktail do not appear to yield detectable FAMEs.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A method of producing fermentable sugars from dried algal biomass comprising the steps of:
   (a) hydrolysing the dried algal biomass with an enzyme composition, the enzyme composition being isolated from *Talaromyces emersonii* which has been grown in a growth medium comprising: (i) carob powder, (ii) a mixture of tea leaves and paper plates, (iii) algae, or (iv) a combination thereof; and
   (b) isolating the sugars from the hydrolysate of step (a).

2. The method as claimed in claim 1 wherein the algal biomass does not undergo chemical or mechanical pretreatment prior to hydrolysis.

3. The method as claimed in claim 1 wherein the carob powder, or a mixture of the tea leaves and paper plates are present in the growth medium in an amount of about 2% (w/v).

4. The method as claimed in claim 1 wherein the algae are present in the growth medium in an amount of about 2% (w/v).

5. The method as claimed in claim 1 wherein cultures grown on algae are prepared from cells grown on carob powder or tea leaves and paper plates in the growth medium in an amount of about 2% (w/v).

6. The method as claimed in claim 1 wherein the hydrolysis is carried out for at least 18 hours.

7. The method as claimed in claim 3 wherein the hydrolysis is carried out for at least 6-24 hours.

8. The method as claimed in claim 1 wherein in step (a) the ratio of the enzyme composition to the dried algal biomass is 0.5 mL enzyme composition diluted from fermentation broth to 50-500 mg algal biomass (dry weight) is used.

9. The method as claimed in claim 1 wherein the hydrolysis is carried out at 65 to 70° C.

10. The method as claimed in claim 1 wherein the hydrolysis is carried out at 67° C.

11. The method as claimed in claim 1 wherein the hydrolysis is carried out at pH 4 to 5.

12. The method as claimed in claim 4 wherein the hydrolysis is carried out at pH 4.5.

13. The method as claimed in claim 1 wherein the hydrolysis is carried out in water.

14. The method as claimed in claim 1 wherein the enzyme and algal biomass mixture is shaken at 120 rpm.

15. Fermentable sugars produced by the method as claimed in claim 1.

16. Oils, including fatty acids and derivatives thereof produced by the method as claimed in claim 1.

17. Proteins, peptides and amino acids produced by the method as claimed in claim 1.

18. Polysaccharides, oligosaccharides and glycoside derivatives produced by the method as claimed in claim 1.

19. Pigments and phenolic substances produced by the method as claimed in claim 1.

20. The method as claimed in claim 1, wherein the dried algal biomass is harvested from brown algae, green algae, red algae or micro algae.

21. The method as claimed in claim 20, wherein the micro algae are selected from the group consisting of a *Laminaria saccharina, Sargussum* sp., *Palmaria palmate* and *Dilsea carnosa*.

22. The method as claimed in claim 20, wherein the micro algae are *Laminaria* spp. harvested in the autumn.

* * * * *